US006758568B2

(12) United States Patent
Valenti (10) Patent No.: US 6,758,568 B2
(45) Date of Patent: Jul. 6, 2004

(54) LIGHT TRAP AND ASSOCIATED LIGHT FOCUSING ASSEMBLY

(75) Inventor: Thomas J. Valenti, Everett, WA (US)

(73) Assignee: The Boeing Company, Seattle, WA (US)

(*) Notice: Subject to any disclaimer, the term of this patent is extended or adjusted under 35 U.S.C. 154(b) by 68 days.

(21) Appl. No.: 10/143,278

(22) Filed: May 10, 2002

(65) Prior Publication Data

US 2003/0210465 A1 Nov. 13, 2003

(51) Int. Cl.[7] .............................................. G02B 27/00
(52) U.S. Cl. ..................... 359/614; 359/613; 359/601
(58) Field of Search ................................. 359/601, 611, 359/613, 614, 503, 506, 851, 853, 896

(56) References Cited

U.S. PATENT DOCUMENTS

| 4,097,751 A | | 6/1978 | Egan et al. ................. 356/211 |
|---|---|---|---|
| 4,929,834 A | * | 5/1990 | Liebson ..................... 250/352 |
| 5,467,189 A | | 11/1995 | Kreikebaum et al. ....... 356/336 |
| 5,479,009 A | | 12/1995 | Jablonski et al. ........... 359/853 |
| 5,537,203 A | | 7/1996 | Carr .......................... 356/236 |
| 5,731,875 A | | 3/1998 | Chandler et al. ........... 356/336 |
| 5,745,293 A | | 4/1998 | Lassalle ..................... 359/614 |

FOREIGN PATENT DOCUMENTS

FR          2088198         1/1972

OTHER PUBLICATIONS

Avian Technologies: Integrating Spheres: Light Traps—aviantechnologies.com (visited May 1, 2002) <http://www.aviantechnologies.com>, 3 pages.
Lapsphere—products—Optional Sphere Accessories—lapsphere.com, (visited Mar. 29, 2002) <http://www.lapsphere.com/products/products.asp?>, 3 pages.
Lapsphere—products—RT–060–SF and RT–060–IG Reflectance/Transmittance Spheres—lapsphere.com, (visited Apr. 19, 2002) <http://www.lapsphere.com/products/products.asp?>, 3 pages.

* cited by examiner

Primary Examiner—Drew A. Dunn
Assistant Examiner—Joshua L Pritchett
(74) Attorney, Agent, or Firm—Alston & Bird LLP (57) ABSTRACT

A light trap includes a light focusing assembly and a light trap assembly. The light focusing assembly includes an access member and an intermediate member. The access member has a frustoconical shape and includes a first end and a second end having a larger cross-sectional area than the first end. The intermediate member defines an internal cavity therethrough. The intermediate member also includes a first end and a second end, with the first end being in optical communication with the second end of the access member. The light trap assembly includes a housing and a conical member. The housing defines an internal cavity that opens through one end thereof. The housing is positioned relative to the intermediate member proximate the second end of the intermediate member. The conical member has a base and an opposing apex, and is disposed within the internal cavity defined by the housing.

22 Claims, 8 Drawing Sheets

LIGHT TRAP AND ASSOCIATED LIGHT FOCUSING ASSEMBLY

FIELD OF THE INVENTION

The present invention relates generally to light traps for absorbing light and, more particularly, to light traps including associated light focusing assemblies to direct light into the light trap.

BACKGROUND OF THE INVENTION

In many optical systems light traps are used to absorb light. For example, light traps can be used to remove the directly transmitted light component in turbidity measurements, to perform specular component subtraction in color measurement, and to calibrate devices used for light related measurements, such as reflectometers. In this regard, calibration of a meter that measures reflection generally involves two steps. During the first step, an object having a highly, almost perfectly reflective surface is inserted in place of a test object. The meter then measures the reflection of light off of the object having the highly reflective surface to thereby establish an upper boundary calibration point to which subsequently measured test objects are compared. During the second step, a light trap having a low reflective surface is inserted in place of a test object, and the reflection of light off of the light trap establishes a lower boundary calibration point to which subsequently measured test objects are compared.

Thus, it is desirable for a light trap to absorb all or substantially all of the light that impinges the light trap. One conventional light trap 10, shown in FIG. 1A and described by French Patent Application No. 2,088,198, comprises an enclosure in the form of a body of revolution that includes a lateral wall 12 with an absorbent internal surface 12a. The light trap also includes an entry member 14 that is disposed longitudinally at one end of the enclosure. The entry member has an internal face 16, an external face 18 and a frustoconical opening 20 through the entry member and coaxial with the enclosure through which a light beam enters the enclosure. The frustoconical opening narrows in the direction from the internal face of the input member to the external face. The entry member includes an inclined surface on the external face around the frustoconical opening adapted to reflect luminous radiation encountering the inclined surface towards an absorbent peripheral surface facing the latter. To direct the light beams toward the absorbent internal surface of the lateral wall, the light trap also includes a conical body 22 attached to a back wall 24 of the light trap and coaxial with the enclosure, where the point of the cone faces the frustoconical opening.

Figure 1A:
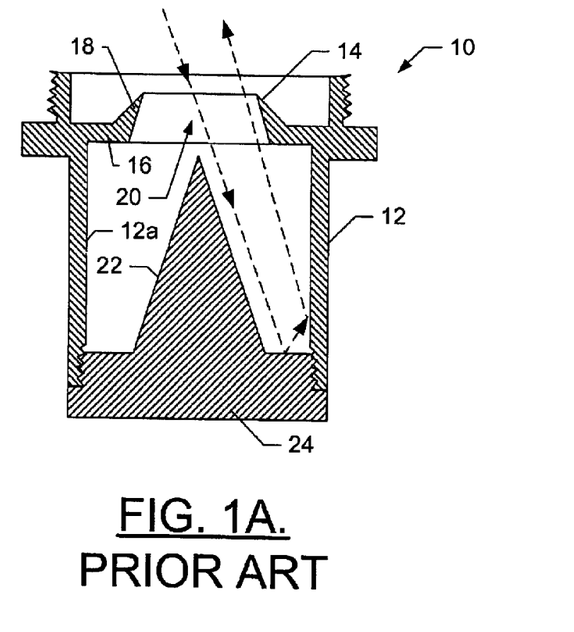
FIGS. 1A, 1B and 1C are cross-sectional illustrations of various conventional light traps.
Figure 1B:
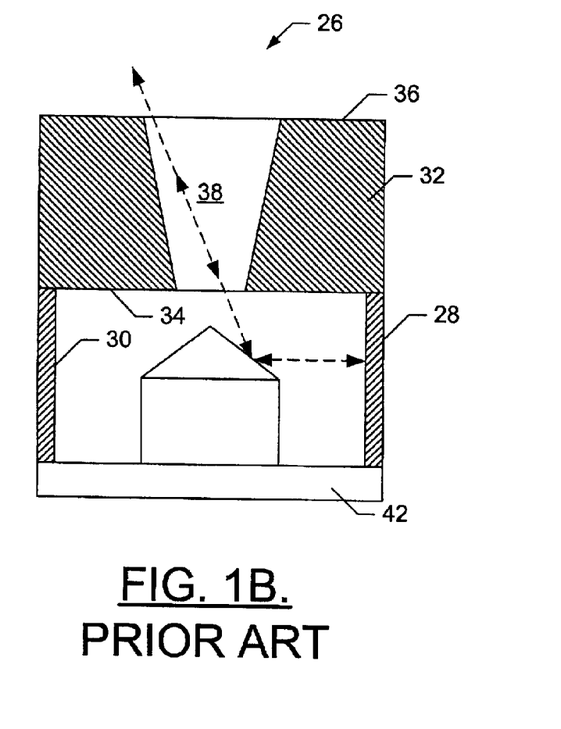

Another conventional light trap is shown in FIG. 1B and described by U.S. Pat. No. 5,745,293. As shown, the light trap 26 of the '293 patent comprises an enclosure that is in the form of a body of revolution and includes a lateral wall 28 with an absorbent internal surface 30. The light trap also includes an entry member 32 that is disposed longitudinally at one end of the enclosure, and includes an internal face 34, an external face 36 and a frustoconical opening 38 through the entry member and coaxial with the enclosure through which a light beam enters the enclosure. At the external face of the entry member, the frustoconical opening has a diameter equal to the diameter of the light beam to be eliminated. Also, the frustoconical opening narrows from the external face towards the internal face of the entry member. Further, a conical body 40 is attached to a back wall 42 of the light trap and is coaxial with the enclosure, where the point of the cone faces the frustoconical opening such that light entering through the opening strikes the cone and is directed toward the absorbent internal surface of the lateral wall.

Figure 1C:
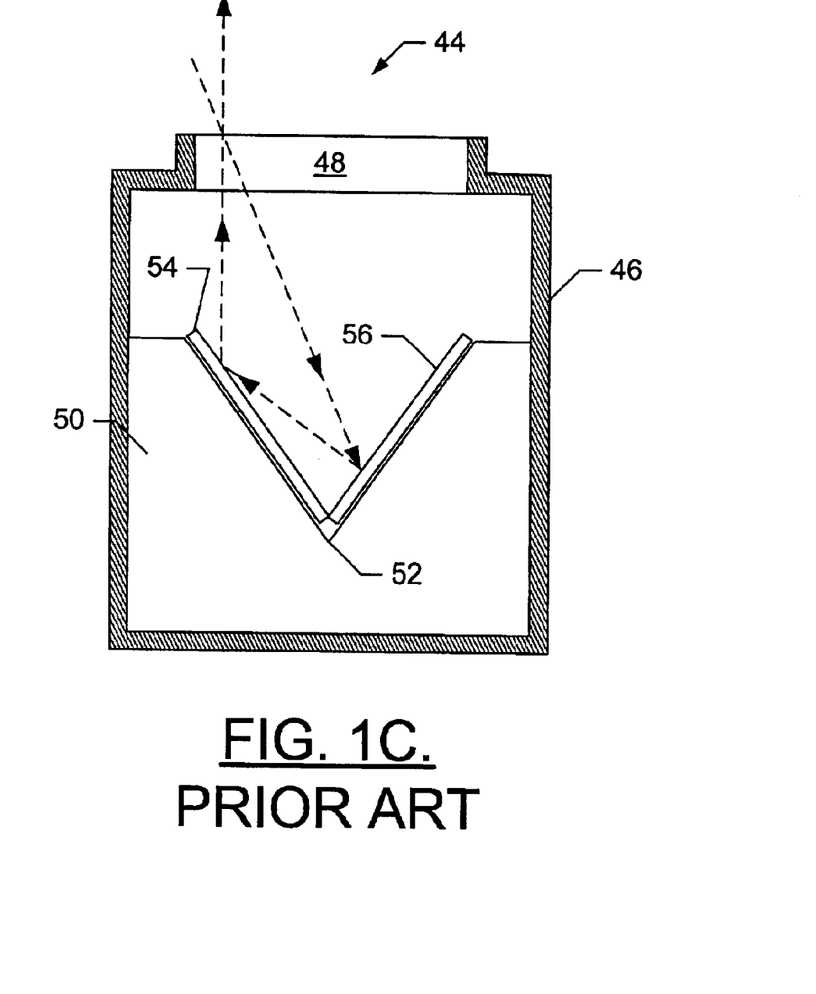

Yet another conventional light trap is shown in FIG. 1C. As shown, the light trap 44 comprises an enclosure having a lateral wall 46 and defining an opening 48 through which a light beam enters the enclosure. Within the enclosure, the light trap includes a wedge-shaped member 50. The wedge-shaped member opens toward the opening and defines a forty-five degree interior angle. The wedge-shaped member includes two faces upon which two pieces of black glass 54 and 56 are disposed. Thus, the pieces of black glass extend from one another toward the opening at a forty-five degree angle.

Conventional light traps, such as those illustrated in FIGS. 1A, 1B and 1C are adequate for absorbing beams of light that enter the light traps parallel to the direction of the lateral walls of the respective light traps. But because of the design of such conventional light traps, conventional light traps will not absorb all of the beams of light that enter the respective light traps. In this regard, at least a portion of some beams of light, particularly those that enter the light traps at an angle close to perpendicular with the lateral walls, will reflect out of the light traps. The escape of light from light traps is disadvantageous. For example, in instances in which a light trap is utilized to calibrate a meter, the escape of light from a light trap skews the lower boundary calibration point.

SUMMARY OF THE INVENTION

In light of the foregoing background, embodiments of the present invention provide an improved light trap and light focusing assembly. In contrast to conventional light traps, the light trap and light focusing assembly of various embodiments of the present invention prevent most, if not all, reflections of light from escaping the light trap. According to one embodiment, the light trap includes a light focusing assembly and a light trap assembly. The light focusing assembly includes an access member and an intermediate member. The access member has a frustoconical shape and includes a first end and a second end having a larger cross-sectional area than the first end. The intermediate member also includes a first end and a second end. In this regard, the intermediate member defines an internal cavity therethrough, and the first end of the intermediate member is in optical communication with the second end of the access member. In another embodiment, the first end of the intermediate member has a larger cross-sectional area than the second end of the intermediate member. In this embodiment, the intermediate member has a frustoconical shape.

The light trap assembly includes a housing and a conical member. The housing defines an internal cavity that opens through one end thereof. In one embodiment, the housing includes a first end and a second end. In this embodiment, the first end of the housing defines the opening to the internal cavity. Also in this embodiment, the first end of the housing has a smaller cross-sectional area than the second end of said housing such that said intermediate member has a frusto-bell shape. In another embodiment, the housing has a cross-sectional area larger than a cross-sectional area of the intermediate member. The housing is positioned relative to the intermediate member proximate the second end of the intermediate member. For example, the housing can be positioned relative to the intermediate member such that the second end of the intermediate member extends into the internal cavity defined by the housing. The conical member, on the other hand, has a base and an opposing apex, and is disposed within the internal cavity defined by the housing. In this regard, the conical member can be disposed such that the apex of the conical member extends into the internal cavity defined by the intermediate member.

To facilitate the absorption of rays of light that enter the light trap, the access member, intermediate member and housing can each include an optically absorbent internal surface. Similarly, the conical member includes an optically absorbent external surface. For example, the internal surfaces of the access member, intermediate member and housing, as well as the external surface of the conical member, can each include an optically absorbent coating.

To absorb light, the access member defines an internal cavity that is capable of receiving at least one ray of light through the first end. Thereafter, the light trap is capable of facilitating specular propagation of the rays of light into the internal cavity of at least one of the access member, the intermediate member and the housing. During propagation of the rays of light, the light trap is capable of absorbing portions of the light to thereby limit propagation of the rays of light out of the internal cavity of the access member after the internal cavity has received the at least one ray of light. As the light trap facilitates specular propagation of the rays of light, the access member, intermediate member and housing can each include an internal surface having a predetermined specular gloss. Similarly, the conical member can include an external surface having the predetermined specular gloss.

BRIEF DESCRIPTION OF THE DRAWINGS

Having thus described the invention in general terms, reference will now be made to the accompanying drawings, which are not necessarily drawn to scale, and wherein:

DETAILED DESCRIPTION OF THE INVENTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Figure 2:
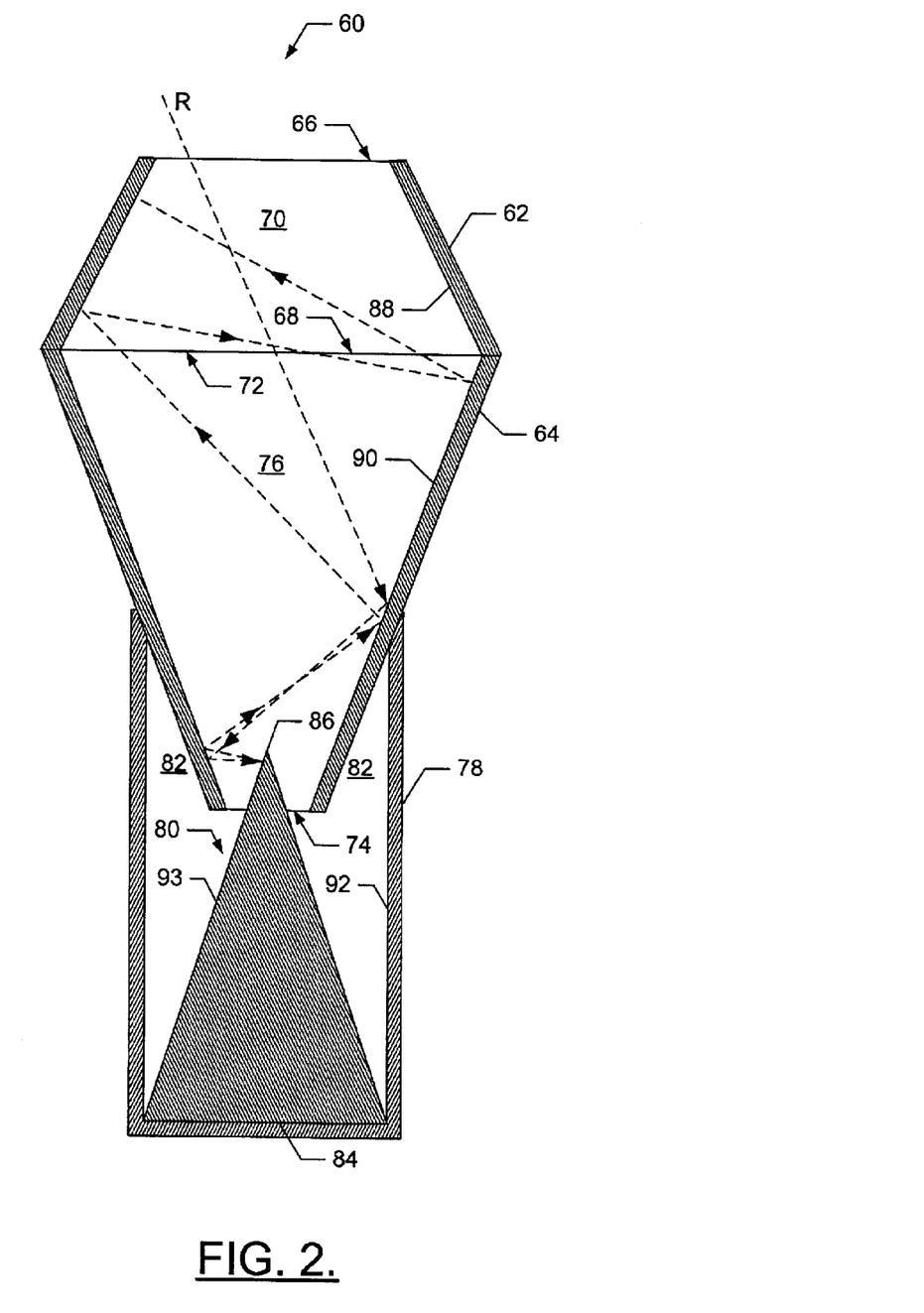
FIG. 2 is a cross-sectional illustration of the light trap of one embodiment of the present invention.
Figure 3A:
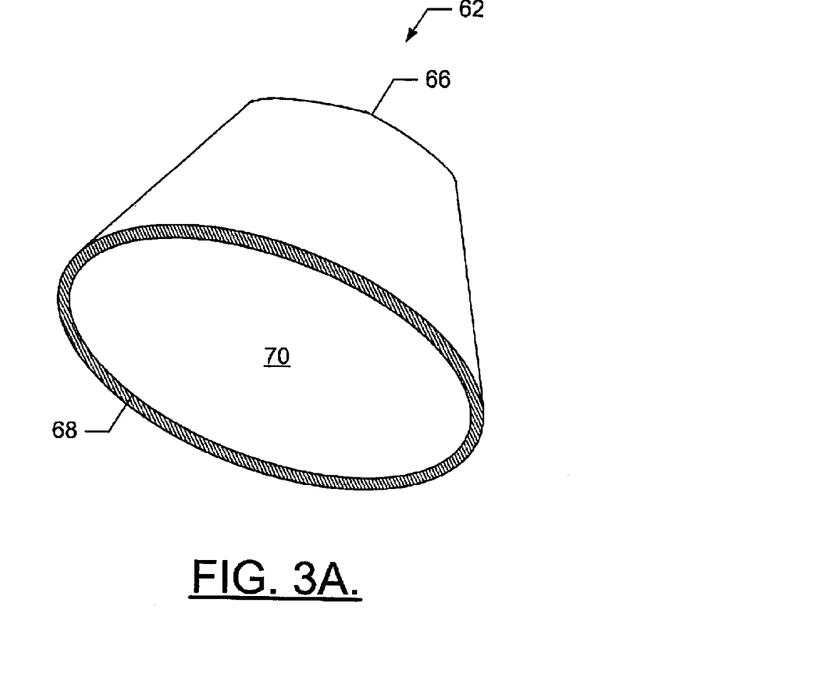
FIGS. 3A and 3B are a perspective view and a cross-sectional view, respectively, of the access member of the light focusing assembly according to one embodiment of the present invention.
Figure 3B:
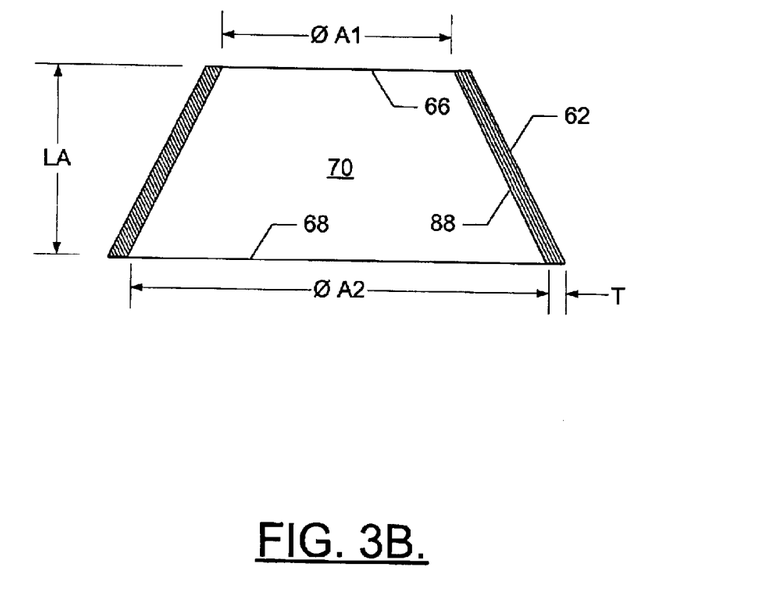

Referring to FIG. 2, a light trap 60 according to one embodiment of the present invention includes a light focusing assembly and a light trap assembly. The light focusing assembly includes an access member 62 and an intermediate member 64. As shown more distinctly in FIGS. 3A and 3B, the access member has a frustoconical shape and includes a first end 66 and a second end 68 that has a larger cross-sectional area than the first end. The access member also defines an internal cavity 70 that extends through the access member. The dimensions of the access member can vary widely depending upon the application of the light trap. For example, according to one embodiment where the first and second ends of the access member have circular cross-sectional areas, the first end can have a diameter ØA1 of approximately 2.25 inches, while the second end can have a diameter ØA2 of approximately 3.5 inches. Further, the access member can have a length LA of approximately 2.0 inches and a wall having a thickness T of approximately 0.2 inches.

Figure 4A:
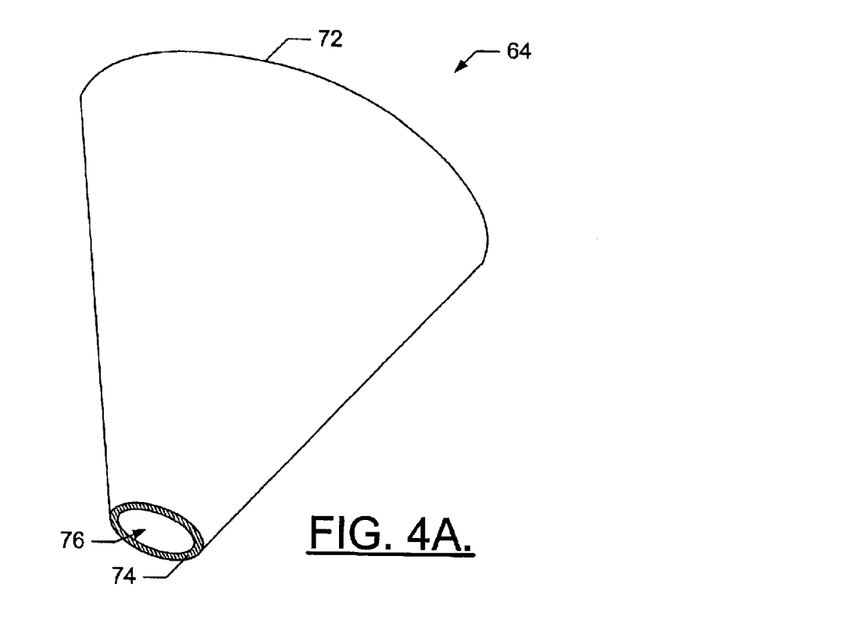
FIGS. 4A and 4B are a perspective view and a cross-sectional view, respectively, of the intermediate member of the light focusing assembly according to one embodiment of the present invention.
Figure 4B:
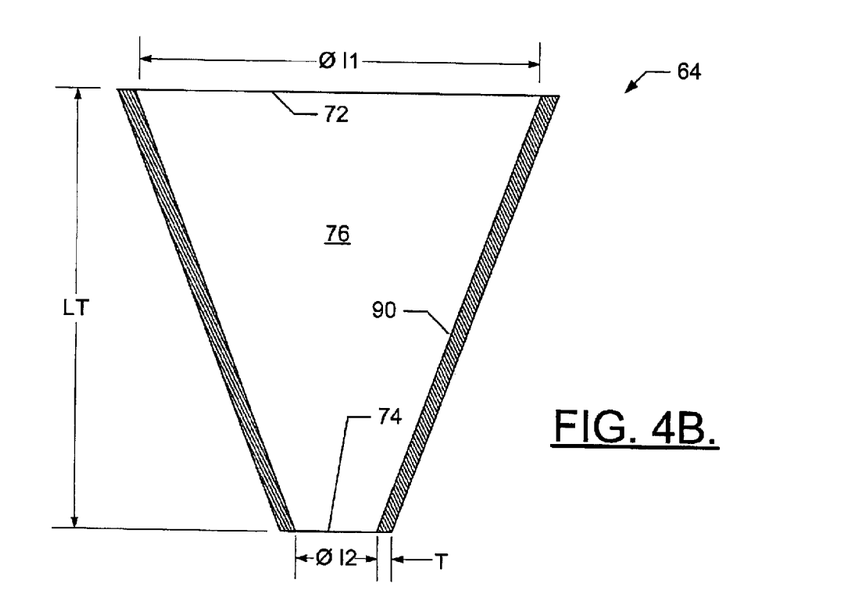

As shown more distinctly in FIGS. 4A and 4B, the intermediate member 64 also includes a first end 72 and a second end 74. And like the access member 62, the intermediate member defines an internal cavity 76 that extends through the intermediate member. In the illustrated embodiment, the first end of the intermediate member has a larger cross-sectional area than the second end and, thus, the intermediate member has a frustoconical shape. Also, the intermediate member can have any of a number of different dimensions depending upon the application of the light trap 60. Typically, however, the first end of the intermediate member is at least as large as the second end 68 of the access member 62 and, most commonly, is equal in size and shape to the second end of the access member. For example, according to one embodiment where the first and second ends of the intermediate member have circular cross-sectional areas, the first end of the intermediate member can have a diameter ØI1 of approximately 3.5 inches, and the second end can have a diameter ØI2 of approximately 0.88 inches. Also, the intermediate member of this embodiment can have a length IL of approximately 5.25 inches, with a wall having a thickness T of 0.2 inches.

To allow rays of light to propagate from the access member 62 to the intermediate member 64, the second end 68 of the access member is in optical communication with the first end 72 of the intermediate member. In this regard, the second end of the access member can be mounted to the first end of the access member such that no light is capable of escaping the light trap at the junction of the access member and the intermediate member. For example, the access member and intermediate member can include mounting portions or flanges (not shown) that extend outwardly from the respective members. In this regard, the mounting portions of the access member and intermediate member can be secured to one another, such as by a screw, pin or the like, to thereby secure the access member to the intermediate member and place the second end of the access member in optical communication with the first end of the intermediate member.

Referring back to FIG. 2, the light trap assembly of the illustrated embodiment includes a housing 78 and a conical member 80. The housing defines an internal cavity 82 that opens through one end of the housing. The housing is positioned relative to the intermediate member 64 proximate the second end 74 of the intermediate member and, in the illustrated embodiment, the intermediate member is positioned relative to the housing such that the second end of the intermediate member extends into the internal cavity of the housing. In this regard, the second end of the intermediate member is in optical communication with the internal cavity of the housing. Thus, like the access member and the intermediate member, to allow rays of light to propagate from the access member 62 to the intermediate member 64, the second end of the intermediate member can be mounted to the housing such that no rays of light are capable of escaping the light trap at the junction of the intermediate member and the housing. For example, the intermediate member and the housing can include mounting portions or flanges (not shown) that extend outwardly from the intermediate member and housing such that the mounting portions of the intermediate member and housing can be secured to one another, such as by a screw, pin or the like.

Figure 5A:
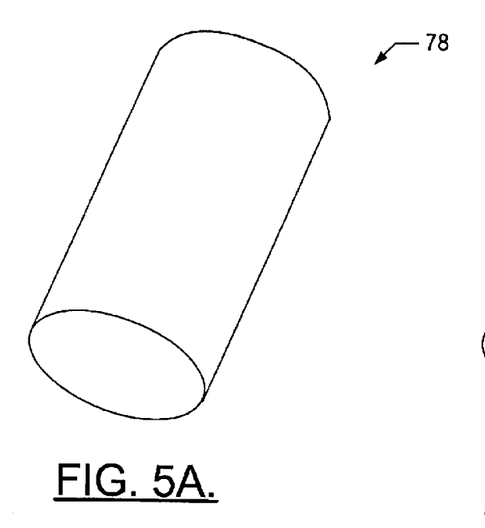
FIGS. 5A and 5B, and 5C are perspective views and a cross-sectional view, respectively, of the housing and conical member of the light trap assembly according to one embodiment of the present invention.
Figure 5B:
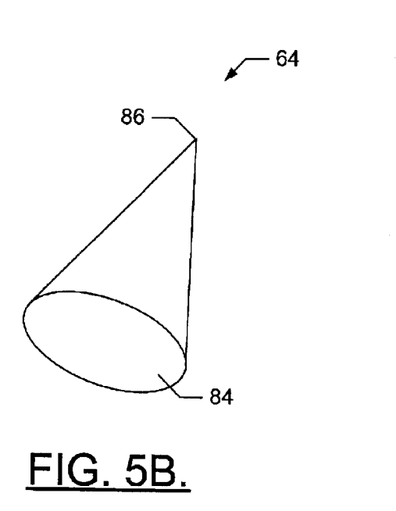
Figure 5C:
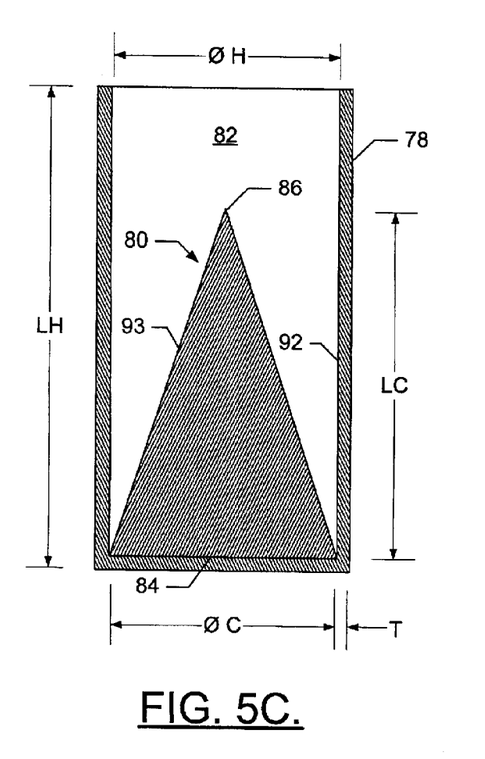

The conical member has a base 84 and an opposing apex 86. The conical member is disposed within the internal cavity 82 of the housing 78. In this regard, the conical member is preferably disposed within the internal cavity of the housing such that the apex of the conical member extends into the internal cavity 68 of the intermediate member 64. As seen more distinctly in FIGS. 5A, 5B and 5C, the housing and the conical member of the light trap assembly of the illustrated embodiment have a circular cross-sectional area, with the housing having a cylindrical shape and the conical member having a cone shape. Like the elements of the light focusing assembly, the housing and conical member can have any of a number of different dimensions depending upon the application of the light trap 60. For example, according to one embodiment, the cross-sectional area of the housing can have a diameter ØH approximately 2.0 inches, while the base of the conical member has a diameter ØC also approximately 2.0 inches. Also, the housing can have a length LH of approximately 5.31 inches, while the conical member has a length LC of approximately 4.0 inches. In addition, the housing can have a wall with a thickness of 0.2 inches. Further, the conical member can comprise a solid object or, if desired, the base of the conical member can at be at least partially hollow to save material.

In operation, the light trap 60 receives rays of light through the first end 66 of the access member 62, of which one ray of light R is illustrated in FIG. 2. After the rays of light enter the light trap, the light propagates through the light trap and initially impinges the internal surfaces 88, 90, 92 of the access member, intermediate member 64 and/or housing 92, and/or the external surface 93 of the conical member 80. As will be appreciated, the surface initially impinged by the light will depend on the angle upon which the light enters the light trap. As the light impinges upon the respective surfaces, the surfaces absorb a significant portion of the light. The remaining portion of the light reflects off of the respective surfaces in a specular manner (as opposed to a diffuse manner).

To promote specular propagation of light beams entering the light trap, the access member 62, intermediate member 64 and housing 78 each includes an internal surface 88, 90 and 92, respectively, having a predetermined specular gloss. Similarly, the conical member 80 includes an external surface 93 that has a predetermined specular gloss. The predetermined specular gloss is preferably high to prevent diffusive propagation of light, and can reach as high as 90 or higher. Further, to promote absorption of the rays of light within the light trap, the internal surfaces of the access member, intermediate member and housing, as well as the external surface of the conical member, are preferably all optically absorbent with a high absorbance.

The internal surfaces 88, 90 and 92 of the access member 62, intermediate member 64 and housing 78, and the external surface 93 of the conical member 80, can comprise any of a number of known optically absorbent surfaces that have the predetermined specular gloss. For example, the access member, intermediate member, housing and conical member can each comprise black glass, which is optically absorbent and typically has a specular gloss at least 95. Alternatively, for example, the access member, intermediate member, housing and conical member can each comprise a metal, such as aluminum. In this embodiment, the internal surface of the access member, intermediate member and housing each includes an optically absorbent coating having a predetermined specular gloss. Similarly, the external surface of the conical member includes an optically absorbent coating having a predetermined specular gloss. For example, one suitable optically absorbent coating is Bumper Black powder coating manufactured by the E. I. du Pont de Nemours and Company of Wilmington, Del., which has a specular gloss of approximately 95.

After the remaining portion of the light reflects off of the respective surfaces, the remaining portion of the light continues to propagate within the light trap 60, and continues to impinge the internal surfaces 88, 90, 92 of the access member, intermediate member 64 and/or housing 92, and/or the external surface of the conical member 80. And as will be apparent, each time the light impinges the respective surfaces, the respective surfaces will absorb a portion of the light, with the remaining light reflecting off of the respective surfaces in a specular manner. In this regard, each time the light impinges a respective surface, less light will remain to reflect toward another surface. Thus, only a small portion, if any, of the light will escape the light trap through the first end 66 of the access member after the light has been accepted into the light trap through the first end of the access member.

Figure 6:
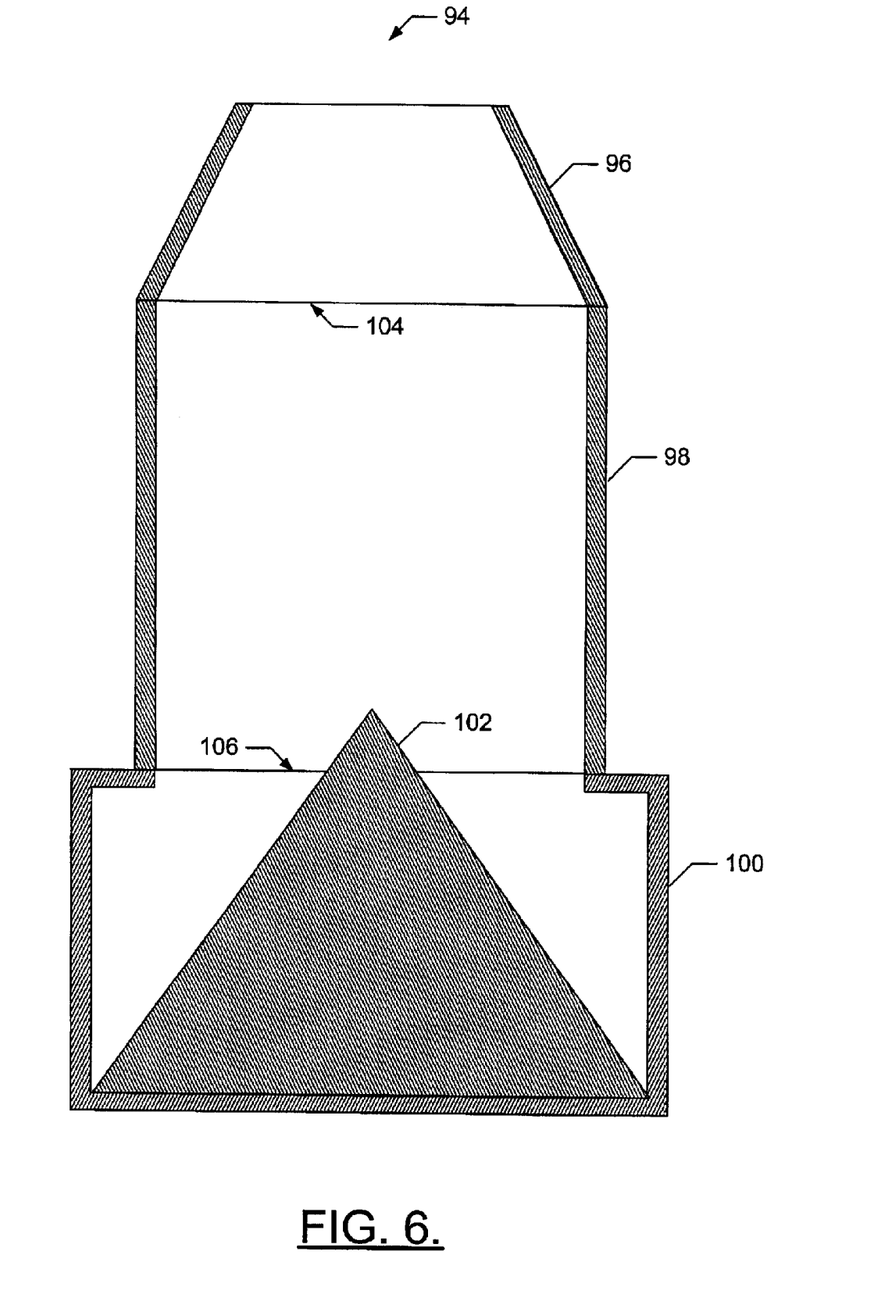
FIG. 6 is a cross-sectional illustration of the light trap of another embodiment of the present invention.

It will be appreciated that the light trap 60 illustrated in FIGS. 2–5 is illustrative of but one embodiment of the light trap of the present invention. In this regard, the intermediate member 76 and housing 78 of the light trap can have any of a number of different configurations without departing from the spirit and scope of the present invention. In this regard, attention is drawn to FIGS. 6 and 7 which illustrate two alternative embodiments of the present invention. As shown in FIG. 6, the light trap 94 of one alternative embodiment includes the light focusing assembly comprising the access member 96 and intermediate member 98. Also, the light trap includes the light trap assembly comprising the housing 100 and the conical member 102. In contrast to the embodiment illustrated in FIGS. 2–5, however, the first and second ends 104 and 106 of the intermediate member have cross-sectional areas that are approximately equal. Thus, the intermediate member of the embodiment illustrated in FIG. 6 has a cylindrical shape. Further, while the housing continues to have a cylindrical shape, the diameter of the cross-sectional area of the housing of the embodiment illustrated in FIG. 6 is larger than the diameter of the cross-sectional area of the first and second ends of the intermediate member.

Figure 7:
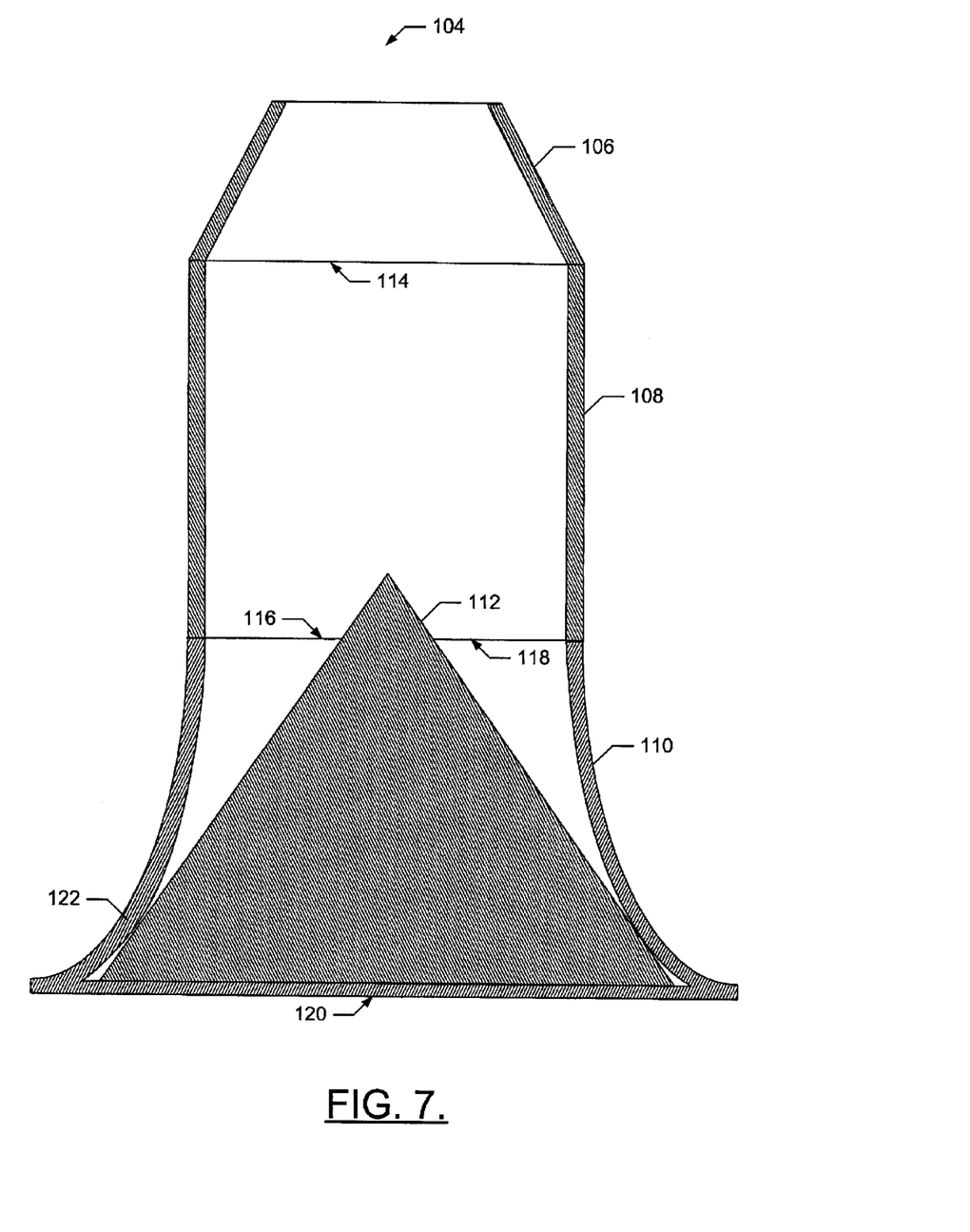
FIG. 7 is a cross-sectional illustration of the light trap of yet another embodiment of the present invention.

As shown in FIG. 7, the light trap 104 of another alternative embodiment includes the light focusing assembly comprising the access member 106 and intermediate member 108. Also, the light trap includes the light trap assembly comprising the housing 110 and the conical member 112. In contrast to the embodiment illustrated in FIGS. 2–5, and similar to the embodiment illustrated in FIG. 6, the first and second ends 114 and 116 of the intermediate member have cross-sectional areas that are approximately equal. Thus, the intermediate member of the embodiment illustrated in FIG. 7 also has a cylindrical shape. In contrast to the embodiment illustrated in FIGS. 2–5, as well as the embodiment of FIG. 6, however, the housing of the embodiment illustrated in FIG. 7 has a first end 118 and a second end 120 that differ in cross-sectional area. In this regard, the first end of the housing has a smaller cross-sectional area than the second end. Also, in embodiments where the ends of the housing have a circular cross-sectional area, the housing has a wall 122 that extends in a concave manner between the ends. Thus, the housing defines a frusto-bell shape.

Many modifications and other embodiments of the invention will come to mind to one skilled in the art to which this invention pertains having the benefit of the teachings presented in the foregoing descriptions and the associated drawings. For example, the access member, intermediate member and/or the light trap assembly can be an integral assembly as opposed to discrete components, if so desired. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A light trap comprising:
    an access member including a first end and a second end having a larger cross-sectional area than the first end;
    an intermediate member including a first end and a second end, wherein said intermediate member defines an internal cavity therethrough, and wherein the first end of said intermediate member is in optical communication with said second end of said access member;
    a housing defining an internal cavity that opens through one end thereof, said housing being positioned relative to said intermediate member proximate the second end of said intermediate member; and
    a conical member having a base and an opposing apex, wherein said conical member is disposed within the internal cavity defined by said housing such that the apex of said conical member extends into the internal cavity defined by said intermediate member.

2. A light trap according to claim 1, wherein said access member, intermediate member and housing each includes an optically absorbent internal surface, and wherein said conical member includes an optically absorbent external surface.

3. A light trap according to claim 1, wherein the internal surfaces of said access member, intermediate member and housing each include an optically absorbent coating, and wherein the external surface of said conical member includes an optically absorbent coating.

4. A light trap according to claim 1, wherein said access member defines an internal cavity that is capable of receiving at least one ray of light through the first end, wherein the light trap is capable of facilitating specular propagation of the at least one ray of light into the internal cavity of an least one of said access member, said intermediate member and said housing, and wherein the light trap is capable of limiting propagation of the at least one ray of light out of the internal cavity of said access member after the internal cavity of said access member has received the at least one ray of light.

5. A light trap according to claim 1, wherein said access member, intermediate member and housing each includes an internal surface having a predetermined specular glass, and wherein said conical member includes an external surface having the predetermined specular gloss.

6. A light trap according to claim 1, wherein said housing is positioned relative to said intermediate member such that the second end of said intermediate member extends into the internal cavity defined by said housing.

7. A light trap according to claim 1, wherein the first end of said intermediate member has a larger cross-sectional area than the second end of said intermediate member such that said intermediate member has a frustoconical shape.

8. A light trap according to claim 1, wherein said housing includes a first end and a second end, wherein the first end of said housing defines the opening to the internal cavity, and wherein the first end of said housing has a smaller cross-sectional area than the second end of said housing such that said intermediate member has a frusto-bell shape.

9. A light trap according to claim 1, wherein said intermediate member has a cross-sectional area smaller than a cross-sectional area of said housing.

10. A light trap according to claim 1, wherein said access member has a frustoconical shape.

11. A light focusing assembly adapted for use with a light trap, wherein the light focusing assembly comprises:
    an access member including a first end and a second end having a larger cross-sectional area than the first end; and
    an intermediate member including a first end and a second end, wherein the first end of said intermediate member is at least as large as the second end of said access member, wherein said intermediate member defines an internal cavity therethrough, and wherein the first end of said intermediate member is in optical communication with the second end of said access member such that light is capable of passing from the second end of said access member through the first end of said intermediate member without first passing through the second end of said intermediate member.

12. A light focusing assembly according to claim 11, wherein said access member and said intermediate member each includes an optically absorbent internal surface.

13. A light focusing assembly according to claim 11, wherein the internal surfaces of said access member and said intermediate member each include an optically absorbent coating.

14. A light focusing assembly according to claim 11, wherein said access member and said intermediate member each includes an internal surface having a predetermined specular gloss.

15. A light focusing assembly according to claim 11, wherein the first end of said intermediate member has a larger cross-sectional area than the second end of said intermediate member such that said intermediate member has a frustoconical shape.

16. A light focusing assembly according to claim 11, wherein said access member has a frustoconical shape.

17. A light trap comprising:
    a light focusing assembly comprising:
        an access member including a first end and a second end having a larger cross-sectional area than the first end; and
        an intermediate member including a first end and a second end, wherein the first end of said intermediate member is at least as large as the second and of said access member, wherein said intermediate member defines an internal cavity therethrough, and wherein the first end of said intermediate member is in optical communication with said second end of said access member such that light is capable of passing from the second end of said access member through the first end of said intermediate member without first passing through the second end of said intermediate member; and a light trap assembly in optical communication with said light focusing assembly, wherein said light trap assembly comprises a housing and a conical member, wherein the housing defines an internal cavity that opens through one end thereof, wherein the conical member is disposed within the enclosure such that when rays of light enter the light trap the conical member is capable of redirecting the at least one ray of light toward at least one of an internal surface of the light focusing assembly and an internal surface of the housing.

18. A light trap according to claim 17, wherein the internal surface of the housing of said light trap comprises an optically absorbent internal surface, wherein the intermediate member and the access member of said light focusing assembly each includes an optically absorbent internal surface, and wherein the conical member of said light trap includes an optically absorbent external surface.

19. A light trap according to claim 17, wherein the access member defines an internal cavity that is capable of receiving at least one ray of light the through the first end, wherein the light trap is capable of facilitating specular propagation of the at least one ray of light into the internal cavity of at least one of the access member, the intermediate member, and the housing, and wherein the light trap is capable of limiting propagation of the at least one ray of light out of the internal cavity of the access member after the internal cavity of the access member has received the at least one ray of light.

20. A light trap according to claim 17, wherein the internal surface of the housing has a predetermined specular gloss, wherein the access member and the intermediate member each includes an internal surface having the predetermined specular gloss, and wherein conical member includes an external surface at least a portion of which has the predetermined specular gloss.

21. A light trap according to claim 17, wherein the access member of said light focusing assembly has a frustoconical shape.

22. A light trap comprising:
a light focusing assembly comprising:
an access member including a first end a second end having a larger cross-sectional area than the first end; and
an intermediate member including a first end and a second end, wherein said intermediate member defines an internal cavity therethrough, and wherein the first end of said intermediate member is in optical communication with said second end of said access member; and
a light trap assembly in optical communication with said light focusing assembly, wherein said light trap assembly comprises a housing and a conical member, wherein the housing defines an internal cavity that opens through one end thereof, wherein the conical member is disposed within the enclosure such that when rays of light enter the light trap the conical member is capable of redirecting the at least one ray of light toward at least one of an internal surface of the light focusing assembly and an internal surface of the housing, wherein the internal surface of the housing includes an optically absorbent coating, wherein the intermediate member and the access member each includes an internal surface having an optically absorbent coating, and wherein the conical member of said light trap includes an external surface having an optically absorbent coating.

* * * * *